United States Patent [19]

Frankel

[11] Patent Number: 4,793,327
[45] Date of Patent: Dec. 27, 1988

[54] DEVICE FOR OPENING A PATIENT'S AIRWAY DURING AUTOMATIC INTUBATION OF THE TRACHEA

[76] Inventor: Alfred R. Frankel, 403 Gulf Way-Apt. 701, Pass-A-Grille Beach, Fla. 33706

[21] Appl. No.: 27,881

[22] Filed: Mar. 19, 1987

Related U.S. Application Data

[63] Continuation-in-part of Ser. No. 820,664, Jan. 21, 1986, Pat. No. 4,672,960, which is a continuation-in-part of Ser. No. 640,843, Aug. 15, 1984, abandoned.

[51] Int. Cl.$^4$ .............................................. A61M 16/00
[52] U.S. Cl. .................. 128/12; 128/200.26; 128/207.14
[58] Field of Search ................ 128/200.26, 3, 10, 12, 128/13, 14, 20, 207.14, DIG. 26

[56] References Cited

U.S. PATENT DOCUMENTS

| | | | |
|---|---|---|---|
| 2,182,390 | 12/1939 | Reardon | 128/12 U X |
| 4,126,127 | 11/1978 | May | 128/13 X |
| 4,306,547 | 12/1981 | Lowell | 128/200.26 X |

Primary Examiner—Alan Cohan
Attorney, Agent, or Firm—Walter J. Monacelli

[57] ABSTRACT

The device described herein consists of a means inserted in the patient's mouth and adjustable to a fixed position for holding the mouth open while an automatic intubation guide is inserted for guiding an endotracheal tube into the patient's trachea. The airway opening device has an opening therein through which the said guide is fed into the mouth and past the pharynx to the esophagus. An endotracheal tube is also fed through the airway opening device and by means of an adaptor or track on the guide the endotracheal tube is inserted into the trachea, after which the guide is withdrawn and the airway opening device is retracted from its fixed position and removed from the mouth.

7 Claims, 5 Drawing Sheets

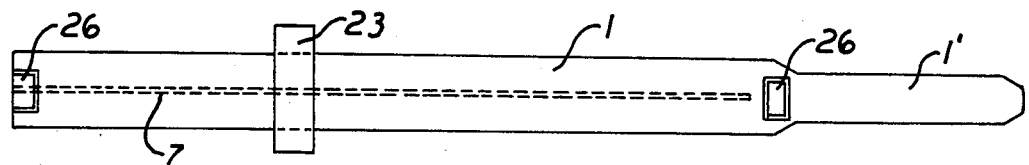
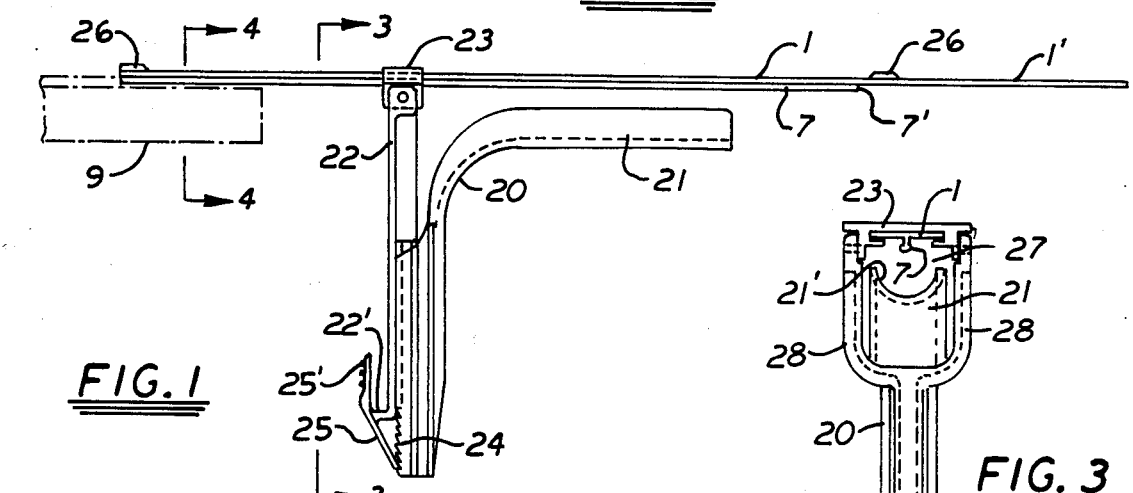
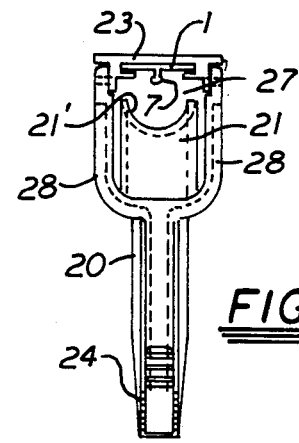
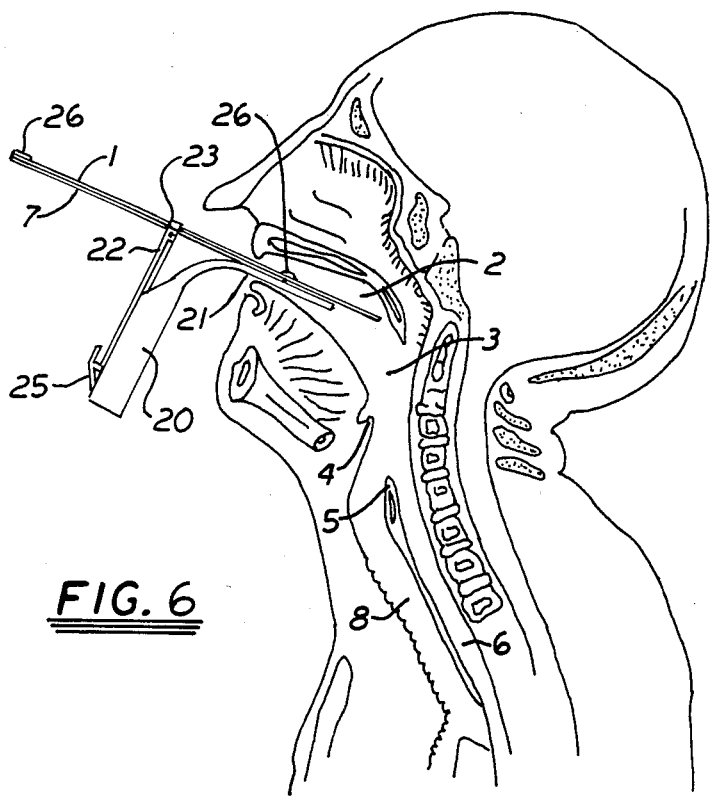
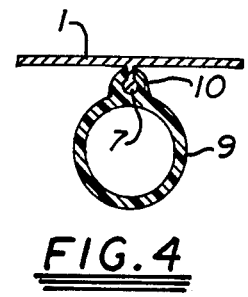
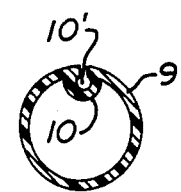
FIG. 1
FIG. 2
FIG. 3
FIG. 4
FIG. 5
FIG. 6

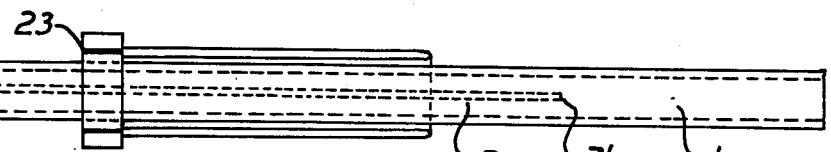
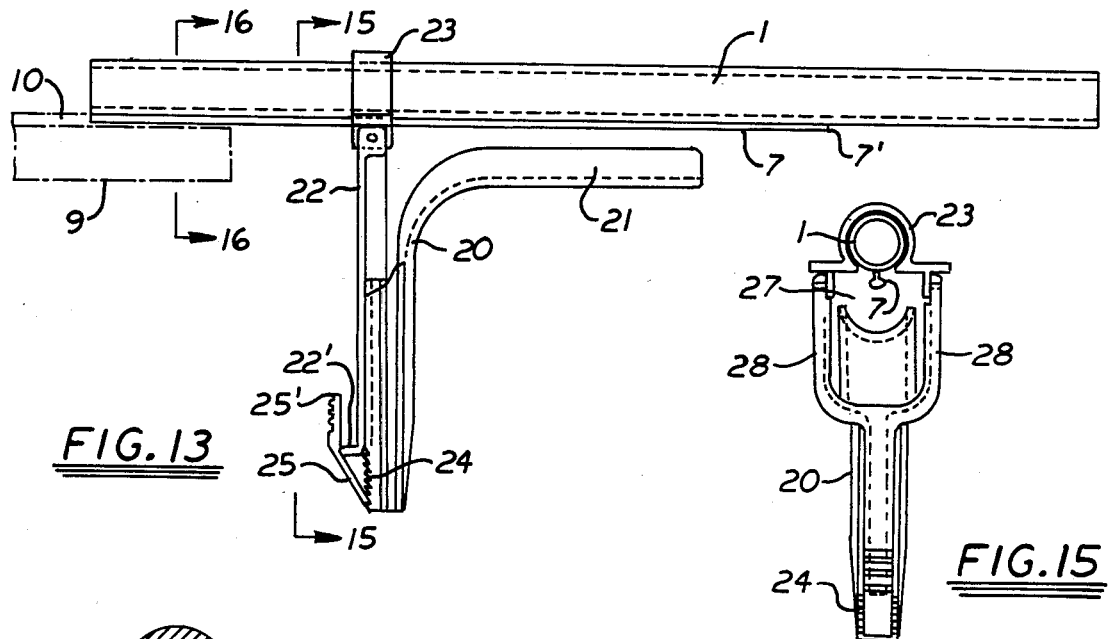
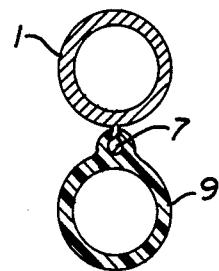
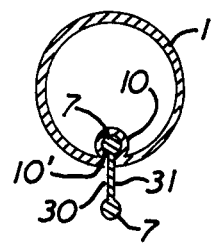
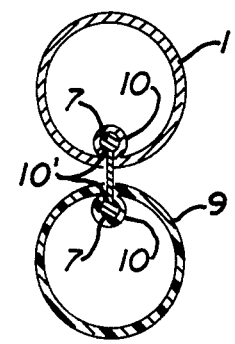
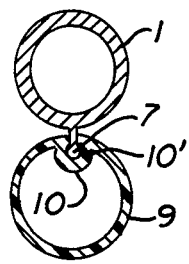

DEVICE FOR OPENING A PATIENT'S AIRWAY DURING AUTOMATIC INTUBATION OF THE TRACHEA

This application is a continuation-in-part of copending application Ser. No. 06/820,664 filed Jan. 21, 1986 now U.S. Pat. No. 4,672,960 issued 6/16/87, which in turn is a continuation-in-part of application Ser. No. 06/640,843 filed Aug. 15, 1984, now abandoned.

BACKGROUND OF THE INVENTION

1. Field of the Invention

This invention relates to a device for holding a patient's airway open during the introduction of a guide to the esophagus and then of an endotracheal tube to and into the trachea. More specifically the airway opening device is provided with a means for holding the device in a fixed position while the guide and the endotracheal tube are passed through and into the mouth and past the pharynx. Still more specifically the guide has a track or adaptor thereon by which the endotracheal tube is guided into a position for entrance into the trachea.

2. Description of the Prior Art

Endotracheal tubes are used to provide relief for patients requiring artificial ventilation. These tubes are presently inserted by a skilled physician using a laryngoscope to displace the epiglottus and allow the physician operator to directly visualize the trachea and the vocal chords and under direct vision insert the endotracheal tube.

Attempts to blindly pass an endotracheal tube will, because of anatomical consideration, generally result in the tube being passed into the esophagus. This principle is used currently in the blind passage of esophageal airways which work by obstructing the esophagus with an inflated balloon. Then with air forced into the mouth and into the upper airway but not able to flow past the obstructing balloon in the esophagus, the air is forced into the trachea and to the lungs. However, an endotracheal tube introduced into the trachea will provide oxygen directly to the lungs and thereby is more efficient.

Applicant's parent applications Ser. Nos. 640,843 and 820,664 disclose a device and process for automatic intubation of an endotracheal tube into a patient's trachea. An esophageal guide having a track or adaptor thereon is introduced into the mouth, past the pharnyx and into the esophagus. Then an endotracheal tube having a means thereon for fitting onto the track or adaptor of the esophegeal guide is affixed to the guide and advanced to the entrance of the trachea where it is released from the tracking guide and advanced to and into the patient's trachea. The turning of the endotracheal tube toward the trachea upon release from the guide is assured by having a substantial linear curvature on the endotracheal tube and having the means for attaching the endotracheal tube to the track on the guide positioned on the outer linear curvature of the endotracheal tube.

It is necessary during this intubation procedure for the operator to use one hand to hold the patient's mouth open and retracting the tongue anteriorly to permit insertion and advancement of the esophageal guide and endotracheal tube. It would be desirable for the operator to have both hands free for use in guiding the esophageal guide and endotracheal tube into the patient's esophagus and track respectively.

OBJECTIVES OF THE INVENTION

It is an objective of this invention to design a device which will facilitate the blind insertion of an endotracheal tube directly into the trachea by medical professionals unskilled in the use of direct laryngoscopy for the emergency insertion of endotracheal tubes.

It is also an objective of this invention to design a device to hold the patient's mouth open while an esophageal guide and a complementary endotracheal tube are passed into the mouth and advanced past the epiglottus, and allow it to disengage itself from the esophageal guide and move anteriorly to enter the trachea.

It is also an objective of this invention to provide a device which will hold the patient's mouth open and retract the tongue anteriorly and to have free both of the operator's hands for manipulation of the esophageal guide and endotracheal tube.

It is also an objective to have a collapsible mouth holding device which may be easily collapsed and removed from the patient's mouth after the esophageal guide and the endotracheal tube have been advanced to the desired positions.

Additional objectives will be obvious from the description of the invention.

SUMMARY OF THE INVENTION

In accordance with the present invention it has been found that the passage of an esophageal guide and an endotracheal tube into the mouth, past the pharynx and into the desired positions is facilitated considerably by the use of the airway opening device of this invention for holding the patient's mouth open during the introduction and advancement of the esophageal guide and endotracheal tube. The airway opening device is designed to move the jaw anteriorly with the tongue and the epiglotus, thereby opening the oral pharynx and the hypopharynx to permit easy passage of the esophageal guide and the endotracheal tube.

First an esophageal guide comprising either a tube, solid rod, including one having a flat oblong cross-section, and having an adaptor or track running along the outside for at least a substantial portion of the length of the esophageal guide is fed through the airway opening device and then introducing an endotracheal tube alongside and on the track of the esophageal guide, this endotracheal tube having an attaching means thereon capable of being fitted to the adaptor or track fixed to the esophageal guide so that the guide will serve to guide the endotracheal tube as the latter is advanced through the mouth holding device and through the mouth and pharynx. As the endotracheal tube is advanced toward the trachea, the attaching means thereof will slide on the adaptor or track of the esophageal guide and be guided thereby.

The adaptor portion on the esophageal guide is of an appropriate length so that it will advance beyond the epiglottus and possibly beyond the dividing or separating wall between the trachea and the esophagus. With the space of the esophageal opening occupied by the guide tube, the advancement of the endotracheal tube will terminate at the dividing wall separating the esophagus and the trachea. Then the endotracheal tube is advanced until it reaches said dividing wall, after which the guide is withdrawn. When the terminus of the adaptor has passed this dividing wall and as the guide is withdrawn, the endotracheal tube will slide off the terminus of the adaptor on the esophageal guide and the linear curvature of the endotracheal tube will turn this tube away from the esophagus and toward the trachea. Further advancement of the endotracheal tube assures entry of this tube into the trachea without having encountered or having been blocked by the epiglottus, and by maintaining the endotracheal tube in the midline the endotracheal tube will be allowed to move anteriorly.

For the esophageal guide the adaptor affixed or incorporated therein is positioned on the inner side of whatever linear curvature is present. With the endotracheal tube the adaptor affixed or incorporated therein is on the outer side of the linear curvature present therein. This arrangement insures that as the endotracheal tube is released from the adaptor on the esophageal guide its linear curvature will turn toward the opening of the tracheal tube.

The position of the distal end of the esophageal guide can be determined or judged by the length of the portion introduced. In this way it is possible to determine that part of the esophageal tube at which the attached adaptor is terminated. As stated previously this terminal of the adaptor is advantageously positioned beyond the epiglottus and before the corniculate cartilage and the arytenoid muscle and cartilage which comprises the separating wall between the trachea and the esophagus. In a particular modification described hereinafter this terminal of the adaptor on the esophageal tube can have a protruding shape which will hook onto or be blocked by this dividing wall. This provides an exact determination of the positioning of this terminal and may also be used to assist in the projection of the endotracheal tube toward the trachea.

The hooking means, the various adaptor means on the esophageal guide and the attaching means on the endotracheal tube, all mentioned above, are described in detail in the above-mentioned parent applications, and these details are incorporated herein by reference thereto. These include the various male and female adaptors on the guide and the complementary adaptors or attaching means described for the endotracheal tube. It is also contemplated that attaching means other than those described in the aforesaid applications may also be used in the practice of this invention.

Once the distal end of the endotracheal tube has entered the trachea the esophageal guide tube can be withdrawn while or even after the endotracheal tube is further advanced into the trachea.

While it is preferred to have the adaptor or track end at a point short of the distal end of the guide, it is possible also to have the track run all the way to the distal end. In such case the operator may depend on blockage of the endotracheal tube by the dividing wall and rely on the withdrawal of the guide to release the endotracheal tube near the entrance to the trachea.

A preferred modification of this invention is one in which the esophageal tube has an oblong cross-section so that it will more truly fit the shape of the esophagus. With the esophageal tube conforming more truly to the cross-section of the esophagus, a track or adaptor positioned in the middle of one of the longer sides of the oblong will position the endotracheal tube which rides on the track more exactly in a position to enter the trachea as decribed more fully hereinafter.

SPECIFIC EMBODIMENTS OF THE INVENTION

The device of this invention may be illustrated by reference to the accompanying drawings in which:

FIG. 1 is a side elevational view of the mouth holding device of this invention with an esophageal guide having a flat oblong cross-section.

FIG. 2 is a top view of the device of FIG. 1.

FIG. 3 is a cross-sectional view of the device of FIGS. 1 and 2 taken at line 3—3 of FIG. 1.

FIG. 4 is a cross-sectional view of the esophageal guide and endotracheal tube of FIG. 1 taken at line 4—4.

FIG. 5 is a cross-sectional view of an endotracheal tube having a modified female adaptor incorporated therein.

FIG. 6 is a side elevational view showing various passageways in a patient's head with part of the mouth holding device of this invention extending partway in the patient's mouth.

FIG. 13 is a side elevational view of the mouth holding device of this invention with an esophageal guide having a circular cross-section.

FIG. 14 is a top view of the device of FIG. 13.

FIG. 15 is a cross-sectional view of the device of FIGS. 13 and 14 taken at line 15—15.

FIG. 16 is a cross-sectional view of FIG. 13 taken at line 16—16.

FIG. 17 is a cross-sectional view similar to that of FIG. 16 in which the endotracheal tube has a modified female adaptor for attachment to the male track on the esophageal guide.

FIGS. 18 and 18a show how an esophageal guide or tube having a female adaptor maybe converted by a double male adaptor to give a guide or tube having a male adaptor and as shown in FIG. 18a how such a converted guide or tube is used with an endotracheal tube having a female adaptor.

Figure 7:
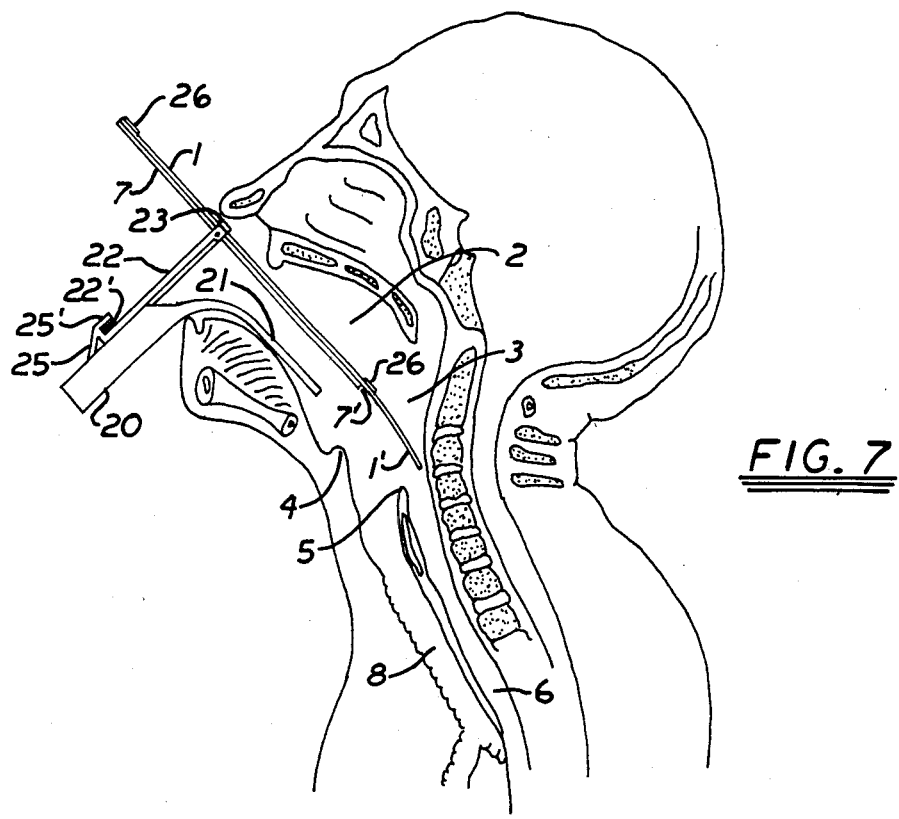
FIG. 7 is a view similar to that of FIG. 6 with the patient's mouth open and the mouth holding device fully inserted into the mouth.

In FIG. 1 the mouth holding device 20 has a lower arm 21 and an upper arm 22 with bracket 23 at the top of arm 22 which has an opening through which esophageal guide 1 is passed, which guide has a male adaptor or track 7 on its underside with terminus 7'. Arm 22 is slidably mounted on the lower portion of arm 21. This is effected by having a pair of vertical tongues (not shown) one on each side of the lower part of arm 20 which fit into a pair of vertical grooves (not shown) one on each side of the lower part of arm 22. The lower portion of arm 21 has a series of notches 24 adapted to receive catch 25 which is swively attached to the lower end of arm 22. When arm 22 is raised catch 25 slides over a series of notches 24 and comes to rest in one of notches 24 to hold arm 22 in its raised position. In order to lower arm 22 it is necessary to press the upper portion 25' of catch 25 to move the catch away from notches 24 so as to permit lowering of arm 22. Catch 25 is swively attached to the lower part 22' of upper arm 22 and is spring actuated to have it press against notches 24 when released. Blocks 26 limit the movement of esophageal guide 1 so as to prevent complete escape of the guide from the opening in bracket 23.

FIG. 2 shows a narrow width 1' of esophageal guide 1 which is an appropriate width to enter the esophagus whereas the width at the wider portion will not permit entry to the esophagus. Therefore the terminus 7' of track 7 is positioned near the entrance to the trachea where the wider portion of the guide is blocked at the entrance to the esophagus.

In FIG. 3 arms 28 are branches of the upper arm 22 which support bracket 23. Lower arm 21 is shown as rounded in the interior section 21' so as to receive in space 27 the circular cross-section of the endotracheal tube. The broken away section at the bottom of upper arm 22 shows notches 24 at the lower end of lower arm 21.

FIG. 4 shows female adaptor 10 of endotracheal tube 9 fitted over adaptor 7 of guide 1.

FIG. 5 shows a modification of an endotracheal tube 9 in which female adaptor 10 is recessed into the tube with its interior 10' adapted to fit onto the male adaptor 7 of guide 1 (not shown here).

FIG. 6 shows the introduction of the mouth holding device 20 in its retracted position into the mouth 2. Guide 1 is extended through bracket 23 ready to be advanced further into the mouth and throat past the epiglottus 4 and into the esophagus 6.

FIG. 7 shows the mouth opening device 20 in its extended position with upper arm 22 raised to hold the mouth open and catch 25 held by one of the notches 24. Guide 1 has been moved inward to where the distal end is past the epiglottus 4 and is at the entrance to the esophagus.

Figure 8:
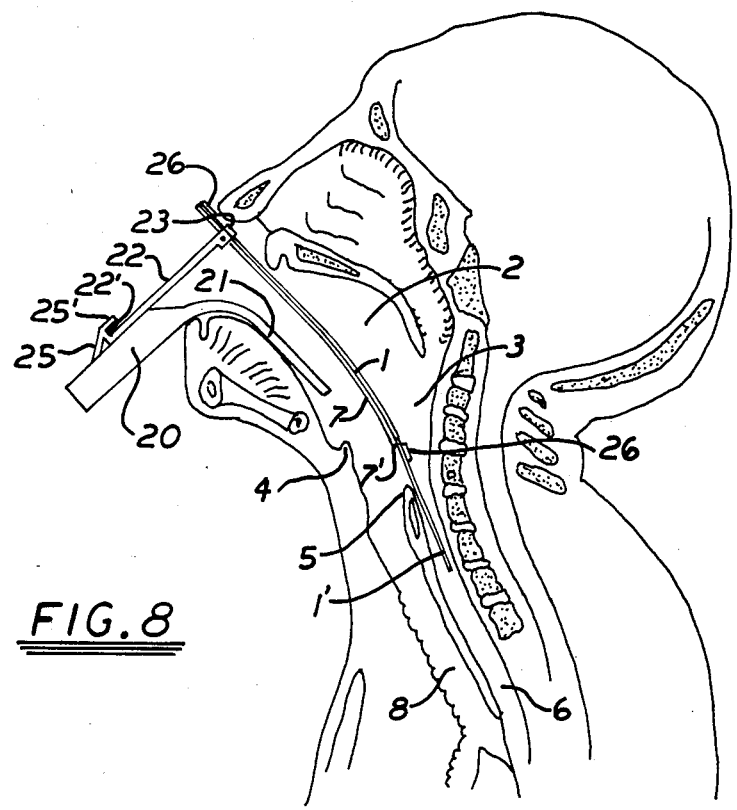
FIG. 8 is a view similar to that of FIGS. 6 and 7 with the esophageal guide advanced into the esophagus.

FIG. 8 shows a view similar to that of FIG. 7 except that the distal end of guide 1 has been moved into the esophagus and the terminus 7' of adaptor 7 on guide 1 is positioned a short distance from wall 5 (the carniculate cartilage and the arytenoid cartilage) which separates the trachea from the esophagus.

Figure 9:
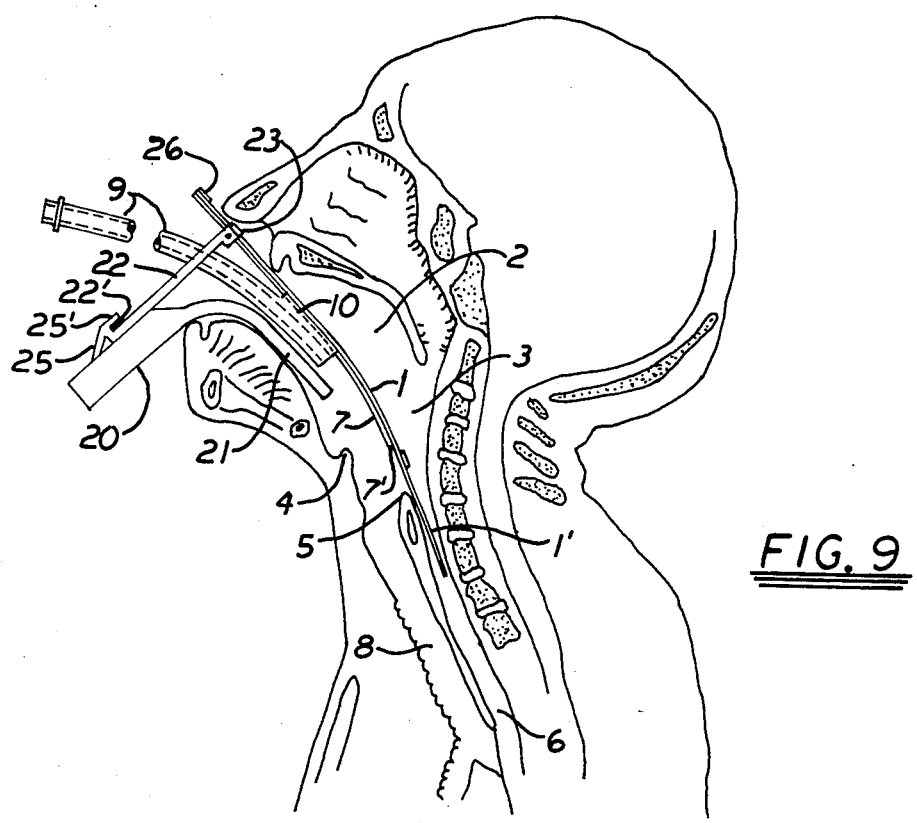
FIG. 9 is a view similar to that of FIGS. 6–8 showing the distal end of an endotracheal tube attached to the track of the esophageal guide.

FIG. 9 is a view similar to that of FIG. 8 except that endotracheal tube 9 is attached by a short sectioned female adaptor 10 to the male adaptor 7 on guide 1.

Figure 10:
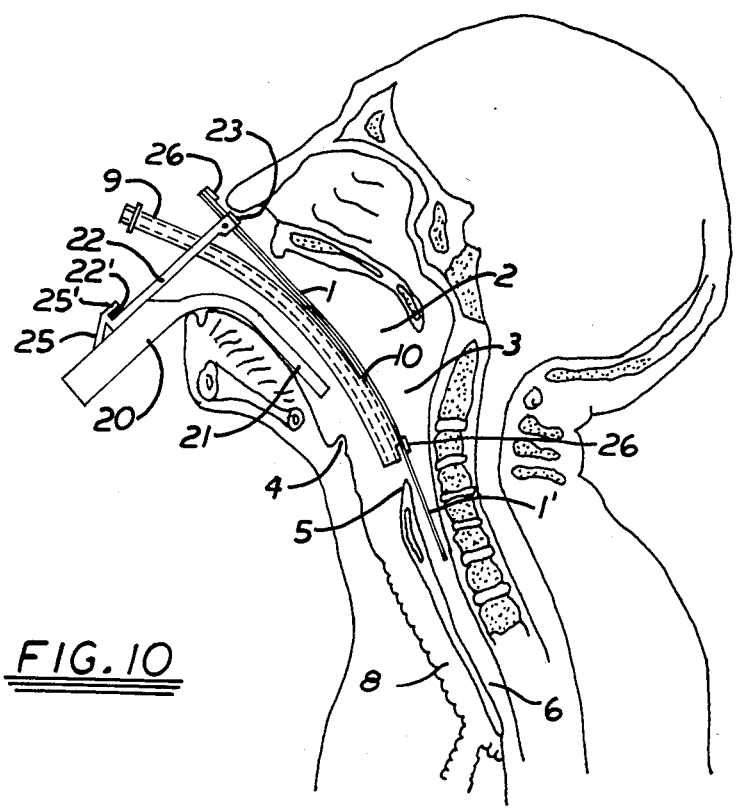
FIG. 10 is a view similar to that of FIGS. 6–9 showing the endotracheal tube advanced to the terminus of the track on the esophageal guide.
Figure 11:
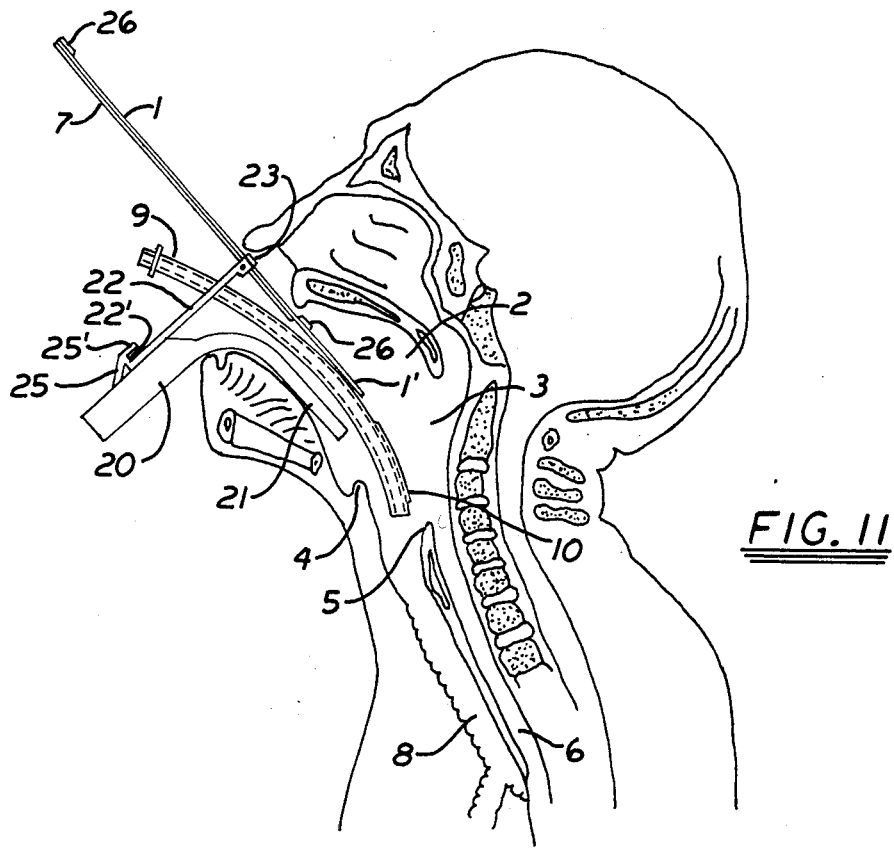
FIG. 11 is a view similar to that of FIGS. 6–10 showing a partial retraction of the esophageal guide leaving the distal end of the endotracheal tube at the entrance to the trachea.

FIG. 10 is a view similar to that of FIG. 9 except that the distal end of endotracheal tube 9 has been advanced to a position just short of wall 5. By subsequent withdrawal of the guide 1 as shown in FIG. 11 the curvature of endotracheal tube 9 turns the tube toward the trachea and away from wall 5.

Figure 12:
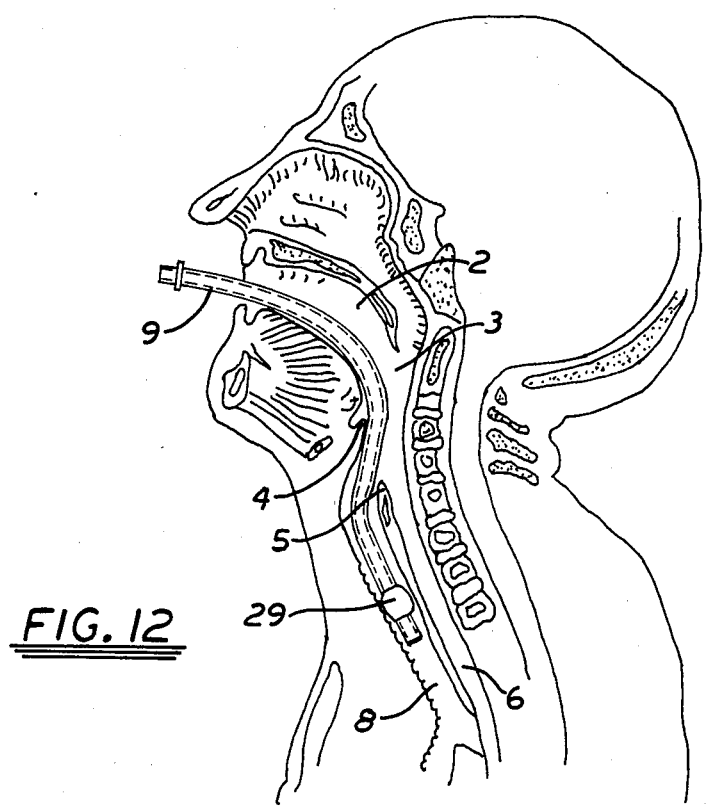
FIG. 12 is a view similar to that of FIGS. 6–11 showing the esophageal guide and the mouth holding device both removed and the endotracheal tube advanced into the trachea.

FIG. 12 shows the complete withdrawal of guide 1 and also mouth holding device 20 (after being retracted to its original shape) as shown in FIG. 6. The endotracheal tube has been advanced well into the trachea and balloon 29 (not previously shown) has been inflated by means of a tiny tube running along the endotracheal tube (either on its interior or exterior) which feeds pressurized air into the balloon.

FIG. 13 is a side elevational view of the mouth holding device as shown in FIG. 1 except that the guide 1 has a circular cross-section as in an esophageal tube with male adaptor 7 on its lower side and adapted to be encompassed by a female adaptor 10 on endotracheal tube 9. Bracket 23 is modified to hold the circular cross-section of the guide.

FIG. 14 is a top view of the device of FIG. 13.

FIG. 15 is a cross-sectional view of the device of FIGS. 13 and 14 taken at line 15—15 of FIG. 13. Space 27 of appropriate size and shape is provided to accommodate the guide of circular cross-section.

FIG. 16 is a cross-sectional view of the guide 1 and endotracheal tube 9 attached to each other and taken at line 16—16 of FIG. 1.

FIG. 17 is a cross-sectional view similar to that of FIG. 16 except that the endotracheal tube 9 has a female adaptor 10 modified from that of FIG. 16.

FIG. 18 shows by cross-sections similar to those of FIGS. 16 and 17 how esophageal guide or tube 1 having a female adaptor 10 with opening 10' is converted by double male adaptor 30, having two male adaptors 7 connected by stem 31, to a guide or tube having a male adaptor extending therefrom. FIG. 18a shows an endotracheal tube 9 with a female adaptor 10 attached to the unoccupied male adaptor 7 of FIG. 18. By withdrawing either the double male adaptor by itself or along with the guide the endotracheal tube may be released.

In the operational device of this invention the forward extending portion of the lower arm 20 is placed on the patient's tongue to hold it depressed during the operation and bracket 23 or guide 1 is used to hold the upper teeth or upper jaw raised once the upper arm 22 is extended to its raised position.

While certain features of this invention have been described in detail with respect to various embodiments thereo, it will of course be apparent that other modifications can be made within the spirit and scope of this invention and it is not intended to limit the invention to the exact details shown except insofar as they are defined in the following claims.

The invention claimed is:

1. A combination of (A) a device for holding a patient's mouth open during automatic intubation of an endotracheal tube comprising (a) a first arm having a lower portion and an upper portion, said upper portion being bent from said lower portion at an angle of approximately 90°; (b) a second arm slidably attached to said lower portion of said first arm on the side of said first arm which is opposite to the bent upper portion thereof, and having a means for locking said second arm in an upward position when said second arm is slid upward from the lower portion of said first arm, said second arm having a lower portion and an upper portion and said upper portion of said second arm having an opening therein which permits the passage of an esophageal guide and also of an endotracheal tube through the upper portion of said second arm; and (c) a means for releasing said locking means to permit the sliding of said second arm from its upward position to a lower position; said device being capable of holding a patient's mouth open by resting the upper portion of said first arm on the patient's tongue and the patient's upper teeth or jaw on the upper portion of said second arm and (B) an esophageal guide and an endotracheal tube inserted in said opening, said endotracheal tube being at least partially and slidably attached to said guide.

2. The device of claim 1 in which said upper portion of second arm has an opening of such a size and shape to accommodate the passage of said guide therethrough and also to accommodate the passage of an endotracheal tube while said endotracheal is at least partially and slidably attached to said guide.

3. The device of claim 2 in which said locking means comprises a combination of a series of notches in the lower potion of said first arm position in an area facing said second arm and a catching means positioned on the lower portion of said second arm, opposite and adjacent to said series of notches, said catching means having a spring means for pressing said catching means toward and into said notches.

4. The device of claim 1, in which said locking means comprises a combination of a series of notches in the lower portion of said first arm position in an area facing said second arm and a catching means positioned on the lower portion of said second arm, opposite and adjacent to said series of notches, said catching means having a spring means for pressing said catching means toward and into said notches.

5. The device of claim 4 in which said catching means has a lever arm attached thereto which by the exertion of pressure thereon will separate said catching means from said notches and thereby release said second arm from a locked relationship with said first arm.

6. The device of claim 3 in which said catching means has a lever arm attached thereto which by the exertion of pressure thereon will separate said catching means from said notches and thereby release said second arm from a locked relationship with said first arm.

7. The device of claim 1 in which said upper portion of said second arm has a second such opening therein.

* * * * *